(12) United States Patent
Miyazaki et al.

(10) Patent No.: US 9,700,220 B2
(45) Date of Patent: Jul. 11, 2017

(54) MAGNETIC RESONANCE IMAGING APPARATUS AND MAGNETIC RESONANCE IMAGING METHOD

(75) Inventors: Mitsue Miyazaki, Mount Prospect, IL (US); Hitoshi Kanazawa, Utsunomiya (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 2184 days.

(21) Appl. No.: 11/790,484

(22) Filed: Apr. 25, 2007

(65) Prior Publication Data
US 2008/0161678 A1  Jul. 3, 2008

(30) Foreign Application Priority Data

Apr. 25, 2006 (JP) ................................ 120382/2006

(51) Int. Cl.
*A61B 5/05* (2006.01)
*A61B 5/026* (2006.01)
(Continued)

(52) U.S. Cl.
CPC ............ *A61B 5/0263* (2013.01); *A61B 5/055* (2013.01); *G01R 33/4824* (2013.01); *G01R 33/5616* (2013.01); *G01R 33/5617* (2013.01); *G01R 33/5635* (2013.01); *A61B 5/7285* (2013.01); *G01R 33/4818* (2013.01); *G01R 33/5614* (2013.01); *G01R 33/5673* (2013.01); *G01R 33/56341* (2013.01); *G01R 33/56509* (2013.01)

(58) Field of Classification Search
USPC ............... 600/407, 410, 411, 415, 419, 420; 424/9.1, 9.3; 5/600, 601; 324/307, 309; 382/100, 128, 131
See application file for complete search history.

(56) References Cited

U.S. PATENT DOCUMENTS

| 6,603,311 B2 | 8/2003 | Ogino |
| 6,781,375 B2 | 8/2004 | Miyazaki et al. |

(Continued)

FOREIGN PATENT DOCUMENTS

| EP | 1408341 A2 | 4/2004 |
| JP | H63(1988)-111845 | 5/1988 |

(Continued)

OTHER PUBLICATIONS

"Periodically Rotated Overlapping ParallEL Lines with Enhanced Reconstruction (PROPELLER) MRI; Application to Motion Correction" by J.G. Pipe (1999).*

(Continued)

*Primary Examiner* — Tse Chen
*Assistant Examiner* — Jason Ip
(74) *Attorney, Agent, or Firm* — Nixon & Vanderhye P.C.

(57) ABSTRACT

A magnetic resonance imaging apparatus includes an imaging condition setting unit, a scan performing unit and a blood flow image generating unit. The imaging condition setting unit sets a sequence accompanying application of a motion probing gradient pulse as an imaging condition. The scan performing unit performs an imaging scan according to the sequence. The blood flow image generating unit generates a blood flow image based on data acquired by the imaging scan.

14 Claims, 7 Drawing Sheets

(51) Int. Cl.
*A61B 5/055* (2006.01)
*A61B 5/00* (2006.01)
*G01R 33/48* (2006.01)
*G01R 33/561* (2006.01)
*G01R 33/563* (2006.01)
*G01R 33/565* (2006.01)
*G01R 33/567* (2006.01)

(56) References Cited

U.S. PATENT DOCUMENTS

| | | |
|---|---|---|
| 6,782,286 B2 | 8/2004 | Miyazaki |
| 6,801,800 B2 | 10/2004 | Miyazaki et al. |
| 7,102,348 B2 | 9/2006 | Zhang et al. |
| 2004/0162483 A1 | 8/2004 | Kimura |
| 2005/0065430 A1* | 3/2005 | Wiethoff et al. ............ 600/413 |

FOREIGN PATENT DOCUMENTS

| | | |
|---|---|---|
| JP | 09-238925 | 9/1997 |
| JP | 2002-534180 | 10/2002 |
| JP | 2003-135430 | 5/2003 |
| JP | 2004-129724 | 4/2004 |
| JP | 2004-242948 | 9/2004 |
| JP | 2005-296663 | 10/2005 |
| JP | 2006-506115 | 2/2006 |
| WO | 00/40989 | 7/2000 |
| WO | 2004/044603 A1 | 5/2004 |

OTHER PUBLICATIONS

"Principles and applications of balanced SSFP techniques" by K. Scheffler and S. Lehnhardt. European Radiology. vol. 13. No. 11. pp. 2409-2418. (2003) (hereinafter as Scheffler et al).*
U.S. Appl. No. 11/524,309, filed Sep. 21, 2006.
David.G. Norris, et al., "On the Application of Ultra-fast RARE Experiments" Magnetic Resonance in in Medicine, vol. 27, 142-164 (1992).
European Search Report dated Dec. 13, 2006 with respect to related Application U.S. Appl. No. 11/524,309.
Miyazaki et al., "Phase-Adjusted Fresh Blood Imaging (PA-FBI) as a Non-Contrast Peripheral MRA Technique", Proceedings of the International Society for Magnetic Resonance in Medicine, 14$^{th}$ Meeting Proceedings, May 6, 2006, p. 1934, XP002411480.
Miyazaki et al., "Peripheral MR Angiography: Separation of Arteries from Veins with Flow-Spoiled Gradient Pulses in Electrocardiography-Triggered Three-Dimensional Half-Fourier Fast Spin-Echo Imaging", Radiology, Oak Brook, IL, US, vol. 227, No. 3, Jun. 2003, pp. 890-896, XP009043796.
Machida et al., "Analysis of N/z Ghosts in Single-Shot Half-Fourier FSE Flow Imaging", Proceedings of the International Society for Magnetic Resonance in Medicine, Seventh Scientific Meeting and Exhibition, May 22, 1999, XP002411481, Philadelphia, Pennsylvania, USA.
Miyazaki et al., "Nonenhanced Peripheral MR Aortography: Diastolic and Systolic ECG-Triggered Moving-Bed Acquisition", Proceedings of the International Society for Magnetic Resonance in Medicine, Ninth Meeting Proceedings Apr. 21, 2001, p. 1923, XP002411482.
JP Office Action dated Jul. 30, 2013 in JP 2012-184500.
Office Action dated Sep. 25, 2012 in JP 2007-115212.
Office Action dated Feb. 12, 2013 in JP 2007-115212.
M. Yui M. Miyazaki, H. Kanazawa, K. Okamoto, "Aortic Arch to Intracranial 3D MRA with t-SLIT 3D-SSFP using a Neurovascular-Attached QD head Speeder Coil," Proc. Int. Soc. Mag. Reson. Med. 12, U.S.A., International Society for Magnetic Resonance in Medicine, Inc., May 15, 2004, p. 2121.
Eric C. Wong, et al., "Velocity Selective Arterial Spin Labeling," Proc. Int. Soc. Mag. Reson. Med. 10, U.S.A., International Society for Magnetic Resonance in Medicine, Inc., May 18, 2002, p. 626.
Office Action dated Jun. 26, 2012 in JP 2007-115212.
Office Action mailed Feb. 13, 2015 in U.S. Appl. No. 13/569,573.
Office Action mailed Sep. 11, 2015 in U.S. Appl. No.13/569,573.
Office Action mailed Apr. 5, 2016 in U.S. Appl. No. 13/569,573.
Miyazaki et al., "Non-Contrast-Enhanced MR Angiography Using 3D ECG-synchronized half-Fourier fast spin echo," 2000, J.Mag. Res.Imag. 12:776-783.
Jiang et al., "Origin and minimization of residual motion-related artefacts in Navigator-corrected segmented diffusion-weighted EPI of the human brain," 2002, Mag. Res.Med. 47:818-822.
Numano et al., "Diffusion weighted three-dimentional MP-RAGE MR Imaging," 2005, Mag.Res.Imaging 23:463-468.

* cited by examiner

MAGNETIC RESONANCE IMAGING APPARATUS AND MAGNETIC RESONANCE IMAGING METHOD

BACKGROUND OF THE INVENTION

1. Technical Field

The present exemplary embodiments relate to an MRI (magnetic resonance imaging) apparatus and a magnetic resonance imaging method which magnetically excites nuclear spins of an object with an RF (radio frequency) signal having the Larmor frequency and reconstruct an image based on an MR (magnetic resonance) signal generated due to the excitation, and more particularly, to a magnetic resonance imaging apparatus and a magnetic resonance imaging method, which performs a non-contrast-enhanced MRA (magnetic resonance angiography) obtaining a blood flow image without using a contrast medium.

2. Related Art

Magnetic resonance imaging is an imaging method which magnetically excites nuclear spins of an object set in a static magnetic field with an RF signal having the Larmor frequency and reconstructs an image based on an MR signal generated due to the excitation.

In the field of magnetic resonance imaging, as a method of obtaining an image of a blood flow, MRA is known. MRI that does not use a contrast medium is referred to as non-contrast-enhanced MRA. As non-contrast-enhanced MRA, an FBI (fresh blood imaging) method which performs in synchronism with an ECG (electrocardiogram) signal to capture a rapid blood flow ejected from the heart, thereby satisfactorily representing a blood vessel has been devised (for example, refer to Japanese Patent Application (Laid-Open) No. 2000-5144).

Such non-contrast-enhanced MRA using the FBI method creates a difference between image data acquired with different delay times of ECG synchronization so that an MRA image in which an artery and a vein are distinguished from each other is obtained. In addition, in the FBI method, a flow-spoiled FBI method in which an artery signal is suppressed during systole by applying a spoiler pulse has been devised. That is, according to the flow-spoiled FBI method, the difference of artery signals during diastole and systole of the cardiac muscle is used for imaging.

Further, in the FBI method, in order to extract a blood flow of low flow velocity, a flow-dephasing method in which a gradient pulse (Gspoil) is applied in a RO (readout) direction, and a dephase pulse or refocusing pulse is applied to a gradient magnetic field pulse has been designed (for example, refer to JP-A-2003-135430). According to the flow-dephasing method, due to the dephase pulse or the refocusing pulse, it is possible to increase the relative signal difference between a signal value from the blood flow of high velocity and a signal value from the blood flow of low velocity. Therefore, it is possible to clearly distinguish the artery and the vein from each other on the basis of the relative signal difference.

That is, in order to distinguish the artery and the vein, it is important to increase the difference between signals during diastole with respect to signals during systole. In order to increase the difference between signals in diastole and systole, it is needed to make intensity of the signal from the blood flow in systole small. However, especially in case of MRA for a lower limb, since flow velocities of both venous blood and arterial blood are slow, it is difficult to distinguish the artery and the vein due to decrease of signal difference between diastole and systole. Accordingly, a gradient pulse having a proper intensity in the RO direction is set, and the blood flow signal from the artery in systole is suppressed by the set gradient pulse. Thus, it is possible to increase a difference of signals from the artery between diastole and systole. In this state, the blood flow signal in diastole is collected. Subtraction processing and/or MIP (maximum intensity projection) processing are performed on the blood flow signals collected in diastole, and only the artery is represented.

Further ECG-prep as a related technology used with FBI method has been devised to measure an appropriate delay time for ECG synchronization (for example, refer to U.S. Pat. No. 6,144,201). The ECG-prep performs an ECG-prep scan which is a preparation scan to decide an appropriate delay time for ECG synchronization previous to an FBI scan for imaging, and subsequently performs the FBI scan with the ECG delay time decided by the ECG-prep scan. The ECG-prep scan obtains plural single shot images at mutually different time phases by acquiring data at gradually changed different delay time from an R wave of an ECG signal. By selecting an image where a blood vessel is depicted appropriately from among the plural images obtained from the ECG-prep scan, an ECG delay time for the FBI scan can be determined. This allows a high-velocity blood flow to be depicted at a time phase corresponding to a lower flow velocity.

In the conventional Flow-Spoiled FBI method, an FASE (fast advanced spin echo) sequence is used as an imaging sequence and a gradient pulse is applied in an RO direction to suppress a blood-flow signal from an artery systole. In a technology, called Flow-Adjusted FBI, a gradient pulse is applied not only in an RO direction but in a PE (phase encode) direction. A gradient pulse application achieves good arteriovenous separation.

However, when a spoiler intensity of a gradient pulse is increased in order to improve arteriovenous separation performance, it is necessary to extend ETS (echo train spacing). As a result, there are problems in that time resolution decreases with an increase in ETS and arteriovenous separation of a high-velocity blood vessel becomes difficult.

In the conventional Flow-dephasing method, since a dephasing pulse is applied to a gradient magnetic field in an RO direction in a scan under the FASE method, a depiction performance of blood vessels depends on a blood vessel direction and a depiction performance accordingly has a limitation.

BRIEF SUMMARY OF THE INVENTION

The present exemplary embodiments have been made in light of conventional situations, and it is an object of the present exemplary embodiments to provide a magnetic resonance imaging apparatus and a magnetic resonance imaging method which make it possible to acquire a blood flow image in a blood vessel which is an imaging target in a more appropriate condition.

The present exemplary embodiments provide a magnetic resonance imaging apparatus comprising: an imaging condition setting unit configured to set a sequence accompanying application of a motion probing gradient pulse as an imaging condition; a scan performing unit configured to perform an imaging scan according to the sequence; and a blood flow image generating unit configured to generate a blood flow image based on data acquired by the imaging scan.

The present exemplary embodiments also provide a magnetic resonance imaging apparatus comprising: an imaging condition setting unit configured to set an imaging condition using a sequence independent from a travel direction of a blood vessel to be a target of a blood flow image; a scan performing unit configured to perform an imaging scan according to the sequence; and a blood flow image generating unit configured to generate a blood flow image based on data acquired by the imaging scan.

The present exemplary embodiment s also provide a magnetic resonance imaging apparatus comprising: an imaging condition setting unit configured to set a sequence as an imaging condition for applying motion probing gradient pulses each having a mutually different intensity to acquire imaging data with each intensity of the motion probing gradient pulses; a preparation scan performing unit configured to perform a preparation scan according to the sequence; and a reference blood flow image generating unit configured to generate blood flow images for a reference based on data corresponding to each intensity of the motion probing gradient pulses, the data being acquired by the preparation scan.

The present exemplary embodiments also provide a magnetic resonance imaging apparatus comprising: an imaging condition setting unit configured to set a data acquisition timing as an imaging condition for acquiring data in a vicinity of a center of k-space at systole and diastole in a heart rate of a heart; a scan performing unit configured to perform an imaging scan according to the imaging condition; and a blood flow image generating unit configured to generate a blood flow image based on data, pieces of the data being acquired at systole and diastole, respectively, by the imaging scan.

The present exemplary embodiments also provide a magnetic resonance imaging apparatus comprising: a scan performing unit configured to perform an imaging scan according to a sequence independent from a travel direction of a blood vessel to be a target subsequently to applying a gradient magnetic field pulse for a flow selection to serve one of a purpose of compensating a flow and another purpose of facilitating flow void effect in a blood vessel of an object; and a blood flow image generating unit configured to generate a non-contrast-enhanced blood flow image of the object based on data acquired by the imaging scan.

The present exemplary embodiments also provide a magnetic resonance imaging apparatus comprising: an imaging condition setting unit configured to set a sequence accompanying application of a flow encode pulse as an imaging condition; a scan performing unit configured to perform an imaging scan according to the sequence; and a blood flow image generating unit configured to generate a non-contrast-enhanced blood flow image based on data acquired by the imaging scan.

The present exemplary embodiments also provide a magnetic resonance imaging method comprising steps of: setting a sequence accompanying application of a motion probing gradient pulse as an imaging condition; performing an imaging scan according to the sequence; and generating a blood flow image based on data acquired by the imaging scan.

The present exemplary embodiments also provide a magnetic resonance imaging method comprising steps of: setting an imaging condition using a sequence independent from a travel direction of a blood vessel to be a target of a blood flow image; performing an imaging scan according to the sequence; and generating a blood flow image based on data acquired by the imaging scan.

The present exemplary embodiments also provide a magnetic resonance imaging method comprising steps of: setting a sequence as an imaging condition for applying motion probing gradient pulses each having a mutually different intensity to acquire imaging data with each intensity of the motion probing gradient pulses; performing a preparation scan according to the sequence; and generating blood flow images for a reference based on data corresponding to each intensity of the motion probing gradient pulses, the data being acquired by the preparation scan.

The present exemplary embodiments also provide a magnetic resonance imaging method comprising steps of: setting a data acquisition timing as an imaging condition for acquiring data in a vicinity of a center of k-space at systole and diastole in a heart rate of a heart; performing an imaging scan according to the imaging condition; and generating a blood flow image based on data, pieces of the data being acquired at systole and diastole respectively by the imaging scan.

The present exemplary embodiments also provide a magnetic resonance imaging method comprising steps of: performing an imaging scan according to a sequence independent from a travel direction of a blood vessel to be a target subsequently to applying a gradient magnetic field pulse for a flow selection to serve one of a purpose of compensating a flow and another purpose of facilitating flow void effect in a blood vessel of an object; and generating a non-contrast-enhanced blood flow image of the object based on data acquired by the imaging scan.

The present exemplary embodiments also provide a magnetic resonance imaging method comprising steps of: setting a sequence accompanying application of a flow encode pulse as an imaging condition; performing an imaging scan according to the sequence; and generating a non-contrast-enhanced blood flow image based on data acquired by the imaging scan.

The magnetic resonance imaging apparatus and the magnetic resonance imaging method as described above make it possible to acquire a blood flow image in a blood vessel which is an imaging target in a more appropriate condition.

DESCRIPTION OF PREFERRED EMBODIMENTS

A magnetic resonance imaging apparatus and a magnetic resonance imaging method according to exemplary embodiments of the present invention will be described with reference to the accompanying drawings.

Figure 1:
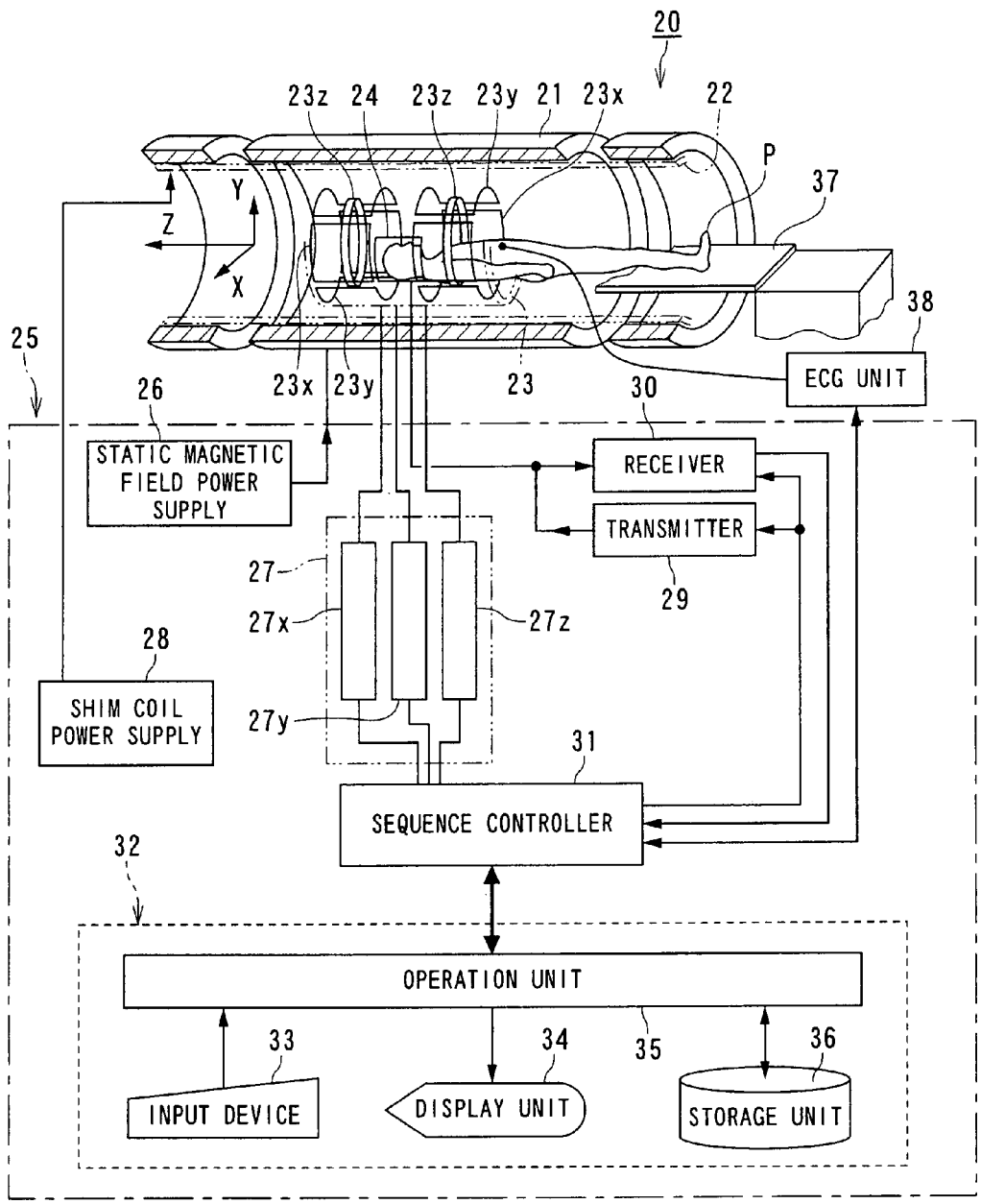
FIG. 1 is a block diagram showing a magnetic resonance imaging apparatus according to an embodiment of the present invention.

FIG. 1 is a block diagram showing a magnetic resonance imaging apparatus according to an exemplary embodiment of the present invention.

A magnetic resonance imaging apparatus 20 includes a static field magnet 21 for generating a static magnetic field, a shim coil 22 arranged inside the static field magnet 21 which is cylinder-shaped, a gradient coil unit 23 and an RF coil 24. The static field magnet 21, the shim coil 22, the gradient coil unit 23 and the RF coil 24 are built in a gantry (not shown).

The magnetic resonance imaging apparatus 20 also includes a control system 25. The control system 25 includes a static magnetic field power supply 26, a gradient power supply 27, a shim coil power supply 28, a transmitter 29, a receiver 30, a sequence controller 31 and a computer 32. The gradient power supply 27 of the control system 25 includes an X-axis gradient power supply 27x, a Y-axis gradient power supply 27y and a Z-axis gradient power supply 27z. The computer 32 includes an input device 33, a monitor 34, a operation unit 35 and a storage unit 36.

The static field magnet 21 communicates with the static magnetic field power supply 26. The static magnetic field power supply 26 supplies electric current to the static field magnet 21 to get the function to generate a static magnetic field in a imaging region. The static field magnet 21 includes a superconductivity coil in many cases. The static field magnet 21 gets current from the static magnetic field power supply 26 which communicates with the static field magnet 21 at excitation. However, once excitation has been made, the static field magnet 21 is usually isolated from the static magnetic field power supply 26. The static field magnet 21 may include a permanent magnet which makes the static magnetic field power supply 26 unnecessary.

The static field magnet 21 has the cylinder-shaped shim coil 22 coaxially inside itself. The shim coil 22 communicates with the shim coil power supply 28. The shim coil power supply 28 supplies current to the shim coil 22 so that the static magnetic field becomes uniform.

The gradient coil unit 23 includes an X-axis gradient coil unit 23x, a Y-axis gradient coil unit 23y and a Z-axis gradient coil unit 23z. Each of the X-axis gradient coil unit 23x, the Y-axis gradient coil unit 23y and the Z-axis gradient coil unit 23z which is cylinder-shaped is arranged inside the static field magnet 21. The gradient coil unit 23 has also a bed 37 in the area formed inside it which is an imaging area. The bed 37 supports an object P. Around the bed 37 or the object P, the RF coil 24 may be arranged instead of being built in the gantry.

The gradient coil unit 23 communicates with the gradient power supply 27. The X-axis gradient coil unit 23x, the Y-axis gradient coil unit 23y and the Z-axis gradient coil unit 23z of the gradient coil unit 23 communicate with the X-axis gradient power supply 27x, the Y-axis gradient power supply 27y and the Z-axis gradient power supply 27z of the gradient power supply 27 respectively.

The X-axis gradient power supply 27x, the Y-axis gradient power supply 27y and the Z-axis gradient power supply 27z supply currents to the X-axis gradient coil unit 23x, the Y-axis gradient coil unit 23y and the Z-axis gradient coil unit 23z respectively so as to generate gradient magnetic fields Gx, Gy and Gz in the X, Y and Z directions in the imaging area.

The RF coil 24 communicates with the transmitter 29 and the receiver 30. The RF coil 24 has a function to transmit a RF signal given from the transmitter 29 to the object P and receive a MR signal generated due to an nuclear spin inside the object P which is excited by the RF signal to give to the receiver 30.

The sequence controller 31 of the control system 25 communicates with the gradient power supply 27, the transmitter 29 and the receiver 30. The sequence controller 31 has a function to storage a pulse sequence describing control information needed in order to make the gradient power supply 27, the transmitter 29 and the receiver 30 drive and generate gradient magnetic fields Gx, Gy and Gz in the X, Y and Z directions and a RF signal by driving the gradient power supply 27, the transmitter 29 and the receiver 30 according to imaging conditions defined by a predetermined pulse sequence stored. The control information above-described includes motion control information, such as intensity, impression period and impression timing of the pulse electric current which should be impressed to the gradient power supply 27. The control information supplied from the sequence controller 31 to the transmitter 29 includes a phase for a transmission and a current intensity of an RF pulse which corresponds to a flip angle for transmission.

The sequence controller 31 is also configured to give raw data to the computer 32. The raw data is complex number data obtained through the detection of a MR signal and A/D conversion to the MR signal detected in the receiver 30.

The transmitter 29 has a function to give a RF signal to the RF coil 24 in accordance with control information provided from the sequence controller 31. The receiver 30 has a function to generate raw data which is digitized complex number data by detecting a MR signal given from the RF coil 24 and performing predetermined signal processing and A/D converting to the MR signal detected. The receiver 30 also has a function to give the generated raw data to the sequence controller 31.

In addition, an ECG unit 38 for acquiring an ECG signal of the object P is provided with the magnetic resonance imaging apparatus 20. The ECG signal detected by the ECG unit 38 is outputted to the computer 32 through the sequence controller 31.

Note that, a PPG (peripheral pulse gating) signal may be acquired instead of an ECG signal. A PPG signal is acquired by detecting a pulse wave of e.g. tip of a finger as an optical signal. When a PPG signal is acquired, a PPG signal detection unit is provided with the magnetic resonance imaging apparatus 20.

The computer 32 gets various functions by the operation unit 35 executing some programs stored in the storage unit 36 of the computer 32. The computer 32 may include some specific circuits instead of using some of the programs.

Figure 2:
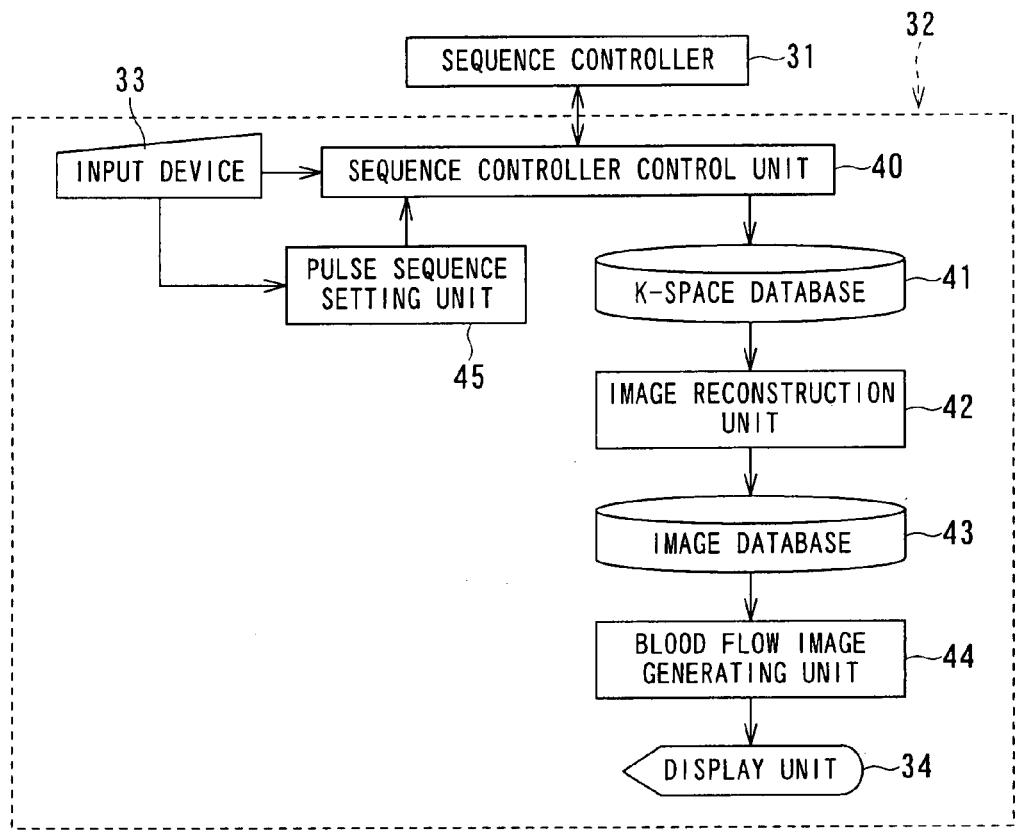
FIG. 2 is a functional block diagram of the computer in the magnetic resonance imaging apparatus shown in FIG. 1.

FIG. 2 is a functional block diagram of the computer 32 in the magnetic resonance imaging apparatus 20 shown in FIG. 1.

The computer 32 functions as a sequence controller control unit 40, a k-space database 41, an image reconstruction unit 42, an image database, a blood flow image generating unit 44 and a pulse sequence setting unit 45 by program.

The sequence controller control unit 40 has a function for controlling the driving of the sequence controller 31 by giving a predetermined pulse sequence acquired from the pulse sequence setting unit 45 to the sequence controller 31 based on information from the input device 33 or another element. Further, the sequence controller control unit 40 has a function for receiving raw data which is k-space data from the sequence controller 31 and arranging the raw data to k-space (Fourier space) formed in the k-space database 41. In addition, the sequence controller control unit 40 is configured to obtain parameters necessary for performing a pulse sequence from the input device 33 or other elements and give them to the sequence controller 31. The sequence controller control unit 40 is also configured to control the sequence controller 31 so that a scan is performed with an ECG synchronous based on an ECG signal obtained by the ECG unit 38 as needed.

Therefore, the k-space database 41 stores each pieces of raw data generated by the receiver 30 as k-space data, and the k-space data is arranged to the k-space formed in the k-space database 41.

The image reconstruction unit 42 has a function for capturing the k-space data from the k-space database 41, performing predetermined image reconstruction processing, such as three dimensional (3D) Fourier transform processing, to the k-space data, reconstructing three dimensional image data of the object P, and writing the image data to the image database 43. Incidentally, intermediate data, such as two dimensional (2D) image data, may be temporarily generated by processing, such as two-dimensional Fourier transform processing, and thereafter the three-dimensional image data may be reconstructed.

Therefore, the image database 43 stores the three-dimensional image data of the object P.

The blood flow image generating unit 44 has a function to read image data from the image database 43 and generate a blood flow image. In case of imaging under the FBI method, an arteriovenous-separated blood flow image can be generated by subtraction processing between arteries-enhanced image data and arteries-suppressed image data acquired in a diastole and a systole of a myocardium respectively in synchronization with ECG based on an ECG signal. Therefore, the blood flow image generating unit 44 has a function to read 3D image data in a diastole and a systole of a myocardium from the image database 43 and cancel vein data by subtraction processing to the read 3D image data to extract artery data as a blood flow image. However, generating a blood flow image without subtraction processing is also possible. In this case, acquiring image data in a systole of a myocardium makes arteriovenous separation easier. Hereinafter, generating a blood flow image with subtraction processing will be described.

In addition, the blood flow image generating unit 44 has a function to perform various processing such as MIP processing for a blood flow image as needed. Further, the blood flow image generating unit 44 has a function to provide a blood flow image generated finally to the display unit 34 to be displayed on it.

Alternatively, the blood flow-image generating unit 44 may be configured to generate a blood flow image from raw data read from the K-space database 41 without the image reconstruction unit 42. Further, an MIP image, an SVR (shaded volume rendering) image or another three-dimensional image may be generated as a blood flow image.

That is, the magnetic resonance imaging device 20 has a function to generate a blood flow image from raw data by the image reconstruction unit 42 and the blood flow image generating unit 44.

The pulse sequence setting unit 45 has a function to set a pulse sequence to acquire a non-contrast-enhanced blood flow image as an imaging condition and provide the set pulse sequence to the sequence controller control unit 40 so that a scan can be performed according to a desired imaging condition.

An arbitrary sequence for a radial scan, a line scan or a spiral scan can be used for an imaging sequence for acquiring a blood flow image. More specifically, an artery and a venation can be represented by using a desired sequence suitable for acquiring a blood flow image, such as a balanced SSFP (steady state free precession) sequence, an FSE (fast spin echo) sequence, an EPI (echo planar imaging) sequence, an FASE sequence, a half-Fourier FSE sequence, as an imaging sequence.

When imaging is performed by using a balanced SSFP sequence or under PROPELLER (Periodically Rotated Overlapping ParallEL Lines with Enhanced Reconstruction) method using an FSE sequence, data can be acquired without depending to directionality of a blood flow to be a target. Therefore, by using a balanced SSFP sequence and an FSE sequence as an imaging sequence, signals from blood vessels traveling in arbitrary directions can be acquired. The balanced SSFP sequence is a sequence for aligning a phase of a transverse magnetization in every repeated excitation or acquiring signals in an SSFP state. The PROPELLER method is a method for radially acquiring data passing the origin in k-space with changing a gradient magnetic field by an FSE sequence. Specifically, in the PROPELLER method, mutually parallel data groups forming a blade are acquired in 1 TR (repetition time) and the k-space is filled with data by rotating the blade every TR.

Note that, a sequence similar to the SSFP sequence may be used for an imaging sequence. An SSFP sequence is a sequence for imaging using a spin echo and a stimulated echo. For example, a sequence for imaging by combining an FID (free induction decay) signal with a spin echo and a stimulated echo may be used as an imaging sequence.

An imaging scan under an imaging sequence can be performed in synchronization with an ECG by using an ECG signal as needed as mentioned above. Performing an imaging scan in synchronization with an ECG makes it possible to acquire image data at a desired cardiac time phase such as a diastole and a systole of a myocardium. Especially in case of imaging under the FBI method, a blood flow image can be obtained by acquiring an echo signal set consisting of plural echo signals in mutually different cardiac time phases such as a diastole and a systole respectively and by subtraction processing to pieces of image data each generated based on the corresponding echo signal set.

In addition, a flow control pre-pulse part can be added to previously to an imaging sequence. The flow control pre-pulse part can change correspondence between a flow velocity of a blood of an object and an image value (a pixel value). In the flow control pre-pulse part, a flow selective gradient magnetic field pulse having a function as a flow control pulse can be applied.

Note that, and another pulse such as a fat saturation pulse may be applied between the flow control pre-pulse part for applying a flow selective gradient magnetic field pulse and an imaging sequence such as an SSFP sequence.

The flow selective gradient magnetic field pulse is categorized into a flow encode pulse for compensating an intravascular blood flow and a flow spoiler pulse facilitating flow void effect.

The flow encode pulse changes a phase of spins (a transverse magnetization) in proportion to a flow velocity of a fluid like a blood. An application of this pulse produces a phase distribution in a transverse magnetization according to a flow velocity. When a longitudinal magnetization recovery pulse is applied subsequently, a distribution of a longitudinal magnetization (a spatial distribution) according to the flow velocity appears. Consequently, background part of a blood flow image is suppressed and blood vessels are enhanced. A flow encode pulse is applied largely in a direction of a blood-flow velocity such as a body axis direction.

A flow spoiler pulse changes a phase of spins (a transverse magnetization) in proportion to a flow velocity of a fluid like a blood as with a flow encode pulse. Specifically, the flow spoiler pulse produces a large phase difference from a slight flow velocity difference in a voxel by producing a phase shift with highly sensitivity to a variation of a flow velocity, and shows an effect to spoil signals from a part where a fluid like a blood has a high flow velocity due to interference effect between spins. It is general for the flow spoiler pulse to use a waveform of a gradient magnetic field pulse by which a phase is shifted to an extent great larger than that by a normal flow encode pulse per unit flow velocity, i.e. a flow encoding amount is large.

When a flow spoiler pulse is used for a flow control pre-pulse part, an application of a longitudinal magnetization recovery pulse subsequently to a pulse application brings a distribution of a longitudinal magnetization (a spatial distribution) according to a flow velocity as in the case of using a flow encode pulse. Accordingly, a scan by an imaging sequence part is performed with a slow recovery of only a longitudinal magnetization in a high-velocity blood flow so that signals from blood vessels are suppressed.

A flow spoiler pulse is applied to suppress signals from a single or plural blood flows which flow in a certain direction or unspecified directions. Therefore, a flow spoiler pulse is often applied in three directions of a slice selection direction (also referred to a slice encode direction), a phase encode direction and a readout direction. An MPG (motion probing gradient) pulse for DWI (diffusion weighted imaging) is an example of flow spoiler pulse.

A type of flow selective gradient magnetic field pulse is determined depending on a purpose of imaging and a method for imaging. An example of practical use is a case where a flow selective gradient magnetic field pulse is applied in an FBI. An FBI is carried out in synchronization with ECG by using an ECG signal and image data is generated from data acquired in a diastole and a systole respectively. A non-contrast-enhanced blood flow image is generated by subtraction processing between pieces of image data corresponding to the diastole and the systole respectively. If a flow encode pulse is applied to arteries to enhance signals from the arteries prior to data acquisition in a diastole while a flow spoiler pulse is applied to arteries to suppress signals from the arteries prior to data acquisition in a systole, subtraction processing can achieve a satisfactory arteriovenous separation to depict the arteries since a difference of intensities of the signals acquired from the arteries in the diastole and the systole increases. In addition, using an SSFP sequence as an imaging sequence for FBI makes it possible to acquire data independent from travel directions of blood vessels.

Another example of practical use, for a purpose of obtaining a non-contrast-enhanced MRA image at a time phase at which a flow velocity is high like as a systole, is a case where a flow encode pulse is applied prior to data acquisition without applying a flow spoiler pulse at another time phase.

In this type of flow control pre-pulse part where a flow selective gradient magnetic field pulse is applied, an excitation pulse, a refocus pulse and a longitudinal magnetization recovery pulse are applied as RF pulses.

Figure 3:
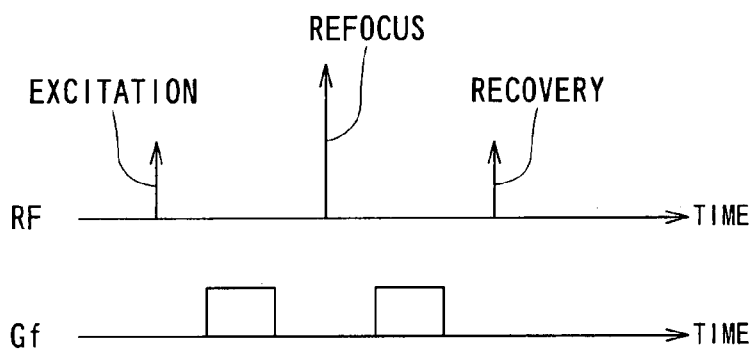
FIG. 3 is a diagram showing an example of a flow control pre-pulse part set in the pulse sequence setting unit shown in FIG. 2.

FIG. 3 is a diagram showing an example of a flow control pre-pulse part set in the pulse sequence setting unit 45 shown in FIG. 2.

In FIG. 3, the abscissa denotes time, RF denotes RF pulses and Gf denotes flow selective gradient magnetic field pulses respectively. As shown in FIG. 3, an excitation pulse, a refocus pulse and a longitudinal magnetization recovery pulse are applied as RF pulses. The longitudinal magnetization recovery pulse is an RF pulse to transform forcibly a transverse magnetization of spins into a longitudinal magnetization. A flip angle of the excitation pulse is set to a desired angle such as 90 degrees or 45 degrees. A flip angle of the longitudinal magnetization recovery pulse is often set to the same angle as that of the excitation pulse. A flip angle of the refocus pulse is set to 180 degrees, for example. Then, two flow selective gradient magnetic field pulses are set to be applied twice before and after the refocus pulse respectively subsequently to an application of the excitation pulse and previously to an application of the longitudinal magnetization recovery pulse.

An imaging sequence such as an SSFP sequence is set to be performed subsequently to the flow control pre-pulse part described above.

Figure 4:
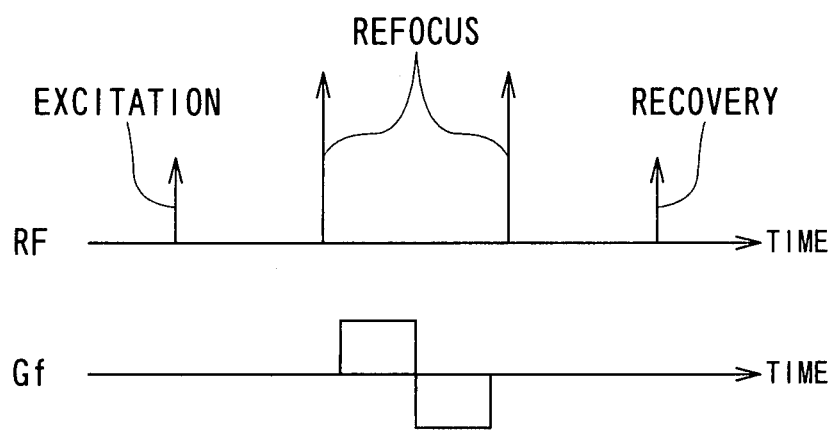
FIG. 4 is a diagram showing another example of a flow control pre-pulse part set in the pulse sequence setting unit shown in FIG. 2.

FIG. 4 is a diagram showing another example of a flow control pre-pulse part set in the pulse sequence setting unit 45 shown in FIG. 2.

In FIG. 4, the abscissa denotes time, RF denotes RF pulses and Gf denotes flow selective gradient magnetic field pulses respectively. As shown in FIG. 4, an excitation pulse, two refocus pulses and a longitudinal magnetization recovery pulse are applied as RF pulses. Then, a flow selective gradient magnetic field pulse is applied between the two refocus pulses. As the flow selective gradient magnetic field pulse, a bipolar pulse of which the area of positive pole side is the same as that of the negative pole side is used.

Whether a flow selective gradient magnetic field pulse shown in FIG. 3 is set or that shown in FIG. 4 is set, similar control effect can be obtained. An intensity and a direction for application of a flow selective gradient magnetic field pulse are set to an appropriate value and direction as imaging conditions respectively. For example, an intensity and a direction for application of a flow selective gradient magnetic field pulse can be determined depending on the travel direction and/or a flow velocity of a target blood flow. Then, a flow selective gradient magnetic field pulse is applied to target vessels carrying blood flows such as blood flows of arteries and blood flows having high flow velocities in an object.

Note that, when an intensity and/or a direction for application necessary to set a flow selective gradient magnetic field pulse are unknown at setting for an imaging sequence, a preparation scan can be performed to determine them as needed. The preparation scan acquires pieces of echo data according to intensities and/or directions for application of plural types of flow selective gradient magnetic field pulses. The preparation scan is preferably set to be a two-dimensional scan for reduction of an imaging period. Based on data, acquired by the preparation scan, corresponding to each intensity and/or application direction of flow selective gradient magnetic field pulses, plural blood flow images for reference are generated respectively and a reference image depicting a blood flow satisfactorily can be selected from the generated plural blood flow images for reference automatically or manually with visual observation. Then, appropriate intensity and/or application direction of a flow selective gradient magnetic field pulse can be determined by selecting a reference image.

Signal values of blood flow data corresponding to respective intensities of flow selective gradient magnetic field pulses can be obtained by performing the preparation scan described above. Therefore, it is also possible to display a graph showing relationship between the intensities of flow selective gradient magnetic field pulses and signal values of data and to determine the intensity of the flow selective gradient magnetic field pulse with referring to the graph. The graph showing the relationship between the intensities of flow selective gradient magnetic field pulses and signal values of data can be created according to the following procedure (algorithm).

First, plural blood flow images for reference corresponding to mutually different intensities of flow selective gradient magnetic field pulses respectively are generated by a preparation scan. In case of generating a subtraction image by imaging, one of the plural blood flow images for reference is set as a standard image and the difference between each blood flow image for reference and the standard image is calculated. Or differences between all two which can be combined of the plural blood flow images for reference are calculated. Consequently, plural subtraction images are generated.

Next, an MIP image is generated by MIP processing in time axis direction to the plural blood flow images for reference or the plural subtraction images in case of performing subtraction processing. Then, a mask image is created by binarizing the MIP image. The created mask image is multiplied by each of the plural blood flow images for reference. Consequently, characteristic amounts corresponding to the respective intensities of the flow selective gradient magnetic field pulses are calculated. Thus, the graph showing the relationship between the respective intensities and the corresponding characteristic amounts, each calculated as described above, of the flow selective gradient magnetic field pulses is created.

For displaying the graph, the pulse sequence setting unit 45 is configured to obtain necessary data from other elements and generate graph information representing the graph to be displayed on the display unit 34.

Without or with displaying the graph, an appropriate intensity of a flow selective gradient magnetic field pulse can be determined by automatically or manually selecting an image with a large amount of flow encode under MIP processing to the reference images in the time axis direction, i.e. an image showing many white parts depicted as blood vessels.

The pulse sequence setting unit 45 has a function to set a sequence for performing a preparation scan as described above. Hereinafter, concrete examples of applying an MPG pulse for DWI as a flow selective gradient magnetic field pulse will be described.

Specifically, the pulse sequence setting unit 45 is configured to set a DWI-Prep sequence for performing a DWI-Prep scan as a preparation scan prior to a sequence for an imaging scan to image a blood vessel. A DWI generates an image with using velocities and directions of diffusion, each serving as a parameter, of water molecules in a tissue by applying an MPG pulse as a pre-pulse.

Figure 5:
FIG. 5 is a diagram showing a performing order of scans to be purposes of pulses sequence set for acquiring a blood flow image by the pulse sequence setting unit shown in FIG. 2.

FIG. 5 is a diagram showing a performing order of scans to be purposes of pulses sequence set for acquiring a blood flow image by the pulse sequence setting unit 45 shown in FIG. 2.

As shown in FIG. 5, a blood flow image can be acquired by performing an imaging scan subsequently to performing a DWI-Prep scan which is a preparation scan. In the imaging scan, a DWI pulse is applied as a pre-pulse. The DWI-Prep scan is performed to determine a DWI intensity necessary for performing the imaging scan. Then, the imaging scan is performed with the DWI intensity determined by performing the DWI-Prep scan and the blood flow image is acquired by performing the imaging scan.

The DWI-Prep sequence to perform the DWI-Prep scan is a sequence by which the DWI sequence and the imaging sequence are repeated plural times. The DWI sequence is a sequence for applying an MPG pulse to determine a DWI intensity. An intensity of an MPG pulse is changed per TR.

It is preferable that the imaging sequence for the DWI-Prep sequence uses a sequence equivalent to the imaging sequence used for the imaging scan as possible.

When the imaging sequence of the DWI-Prep sequence is set to acquire two-dimensional data, it is possible to reduce an image processing throughput and an imaging period in the DWI-Prep scan. However, a three-dimensional image may be acquired under the DWI-Prep scan by setting a three-dimensional sequence for the imaging sequence of the DWI-Prep sequence.

Figure 6:
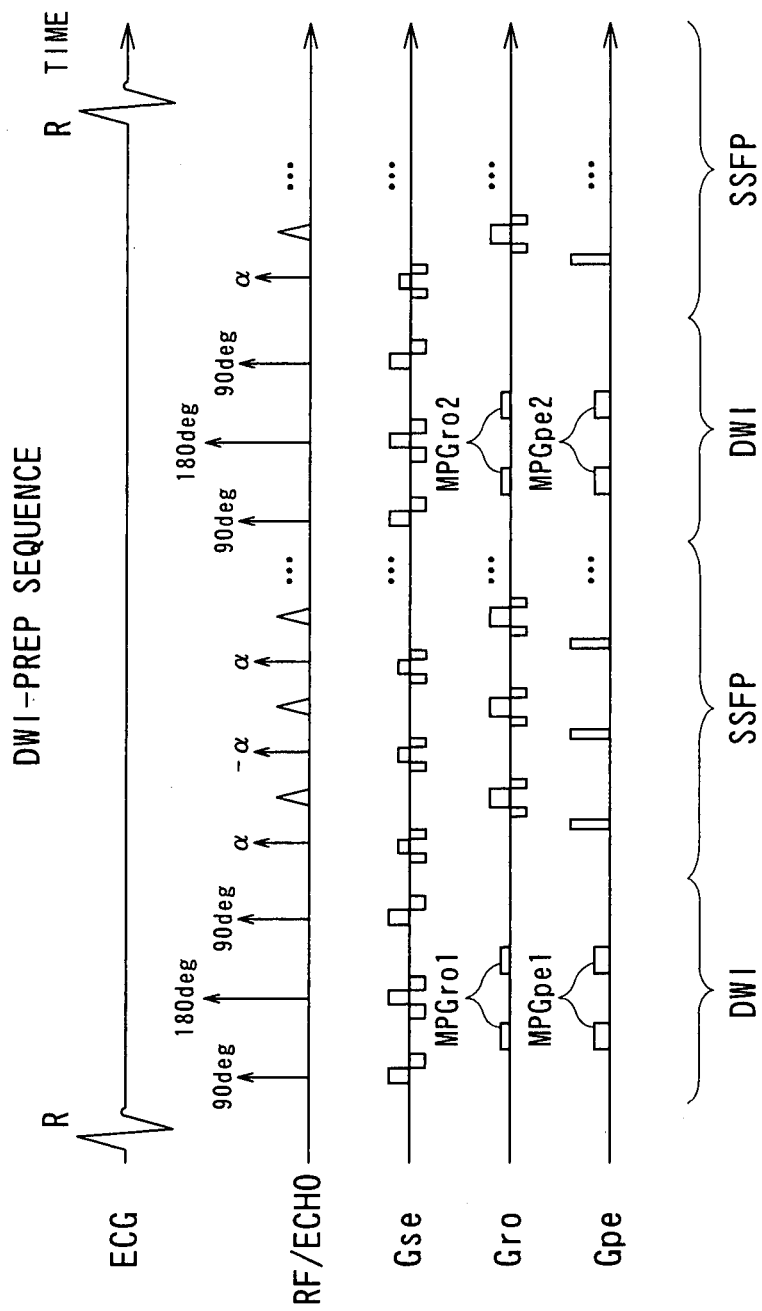
FIG. 6 is a diagram showing an example of a DWI-Prep sequence set in the pulse sequence setting unit shown in FIG. 2.

FIG. 6 is a diagram showing an example of a DWI-Prep sequence set in the pulse sequence setting unit 45 shown in FIG. 2.

In FIG. 6, ECG denotes an ECG signal, RF/ECHO denotes RF signals and ECHO data, Gse denotes a gradient magnetic field for slice encoding, Gro denotes a gradient magnetic field for readout and Gpe denotes a gradient magnetic field for phase encoding respectively. The pulse sequence setting unit 45 sets a DWI-Prep sequence shown in FIG. 6, for example. FIG. 6 shows an example of setting a balanced SSFP sequence for an imaging sequence of the DWI-Prep sequence. Therefore, subsequently to a DWI sequence, the balanced SSFP sequence is set. In addition, subsequently to the balanced SSFP sequence, the next DWI sequence having a changed MPG pulse intensity is set.

The DWI-Prep sequence consisting of the DWI sequence and the balanced SSFP sequence is performed in synchronization with an ECG signal by using an R wave of the ECG signal as a trigger, for example. The Balanced SSFP sequence is preferably set to a single shot sequence suitable for acquiring a blood flow image and an α° pulse and a −α° pulse are applied repeatedly according to the number of pieces of echo data to be acquired. Further, a pulse for various purposes (not shown) such as a fat saturation pulse is applied prior to the first α° pulse as needed.

Then, a DWI sequence is set prior to the balanced SSFP sequence for echo data acquisition. In the DWI sequence, a 90-degree excitation pulse, a subsequent 180-degree refocus pulse and a subsequent 90-degree longitudinal magnetization recovery pulse are applied as RF signals. Each flip angle and flop angle of an excitation pulse, a refocus pulse and a longitudinal magnetization recovery pulse may be set to other angles respectively. Further, MPG pulses are applied before and after the 180-degree refocus pulse as gradient magnetic field pulses. The MPG pulses are applied in necessary directions of a slice encode direction, a readout direction and a phase encode direction. The DWI sequence in FIG. 6 shows an example that a readout direction MPG pulse (MPGro1) and a phase encode direction MPG pulse (MPGpe1) are applied while a slice encode direction MPG pulse (MPGse1) is not applied. Then, echo data is acquired by applying the α° and −α° pulses and the gradient magnetic field pulse of the balanced SSFP sequence with spins dispersed (spoiled) due to diffusion of water molecules in tissues by applying the MPG pulses.

Further, when necessary echo data is acquired after applying the MPG pulse, a 90-degree excitation pulse and a subsequently 180-degree refocus pulse are applied again as RF signals. Then, MPG pulses MPGro2, MPGpe2 with changing intensities are applied before and after the 180-degree refocus pulse again. Thus, similarly, echo data is acquired by applying the α° and −α° pulses and the gradient magnetic field pulse of the balanced SSFP sequence again with spins dispersed (spoiled) due to diffusion of water molecules in tissues by applying the MPG pulses each having a different intensity.

This application of the MPG pulses and echo data acquisition are repeatedly performed by the number of intensities of the MPG pulses.

That is to say, the DWI-Prep sequence is a sequence for single shot multi DWI imaging which performs imaging by a single nuclear magnetic excitation and applies an MPG pulse plural times with changing a DWI intensity, i.e. an intensity of the MPG pulse.

The intensities of an MPG pulse can be changed arbitrarily in three axis directions of a slice direction, a readout direction and a phase encode direction depending on travel directions of blood vessels to be depicted. Therefore, MPG pulses can be applied in one axis direction or two axis directions as well as the example in FIG. 6. For example, when travel directions of blood vessels are three axis directions, the intensities of the MPG pulses can be changed to be equivalent to each other in the three axis directions. When a travel direction of blood vessels is known and particular, the intensities of the MPG pulses can be changed to be different from each other in three axis directions depending on the travel direction of the blood vessels so as to achieve a satisfactory arteriovenous separation in the travel direction of the blood vessels.

By changing the intensities of the MPG pulses arbitrarily in three axis directions depending on the travel direction of the blood vessels in the DWI-Prep sequence as described above, setting intensities of an MPG pulse for an imaging sequence can be variable in three axis directions depending on the travel direction of the blood vessels.

The intensities of the MPG pulse in a phase encode direction and a read out direction are changed in the example shown in FIG. 6. Note that, the intensity of the MPG pulse in the phase encode direction is set to be larger than that in the read out direction. The intensity of the MPG pulse in a slice direction is set to zero. If the intensities of the MPG pulse are set as described above, appropriate intensities of the MPG pulse can be determined to differentiate signals in blood vessels traveling in the phase encode direction and the read out direction satisfactorily.

Figure 7:
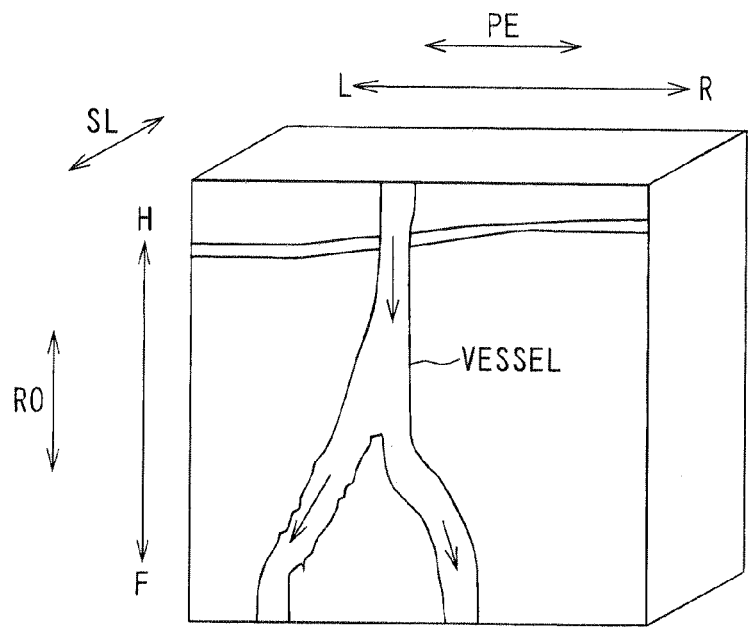
FIG. 7 is a diagram showing an example of a travel direction of a blood vessel referred to by the pulse sequence setting unit shown in FIG. 2 at setting an intensity of an MPG pulse.

FIG. 7 is a diagram showing an example of a travel direction of a blood vessel referred to by the pulse sequence setting unit 45 shown in FIG. 2 at setting an intensity of an MPG pulse.

For example, as shown in FIG. 7, a blood is assumed to flow in a body-axis (HF: head feet) direction when a coronal section is imaged. In this case, if the DWI-Prep sequence is set so that the intensity of the MPG pulse in the HF direction which is a blood flow direction, i.e. an RO direction, is set to be larger than that in a PE direction which is an RL (right left) direction perpendicular to the HF direction while an MPG pulse having a slight intensity is applied in an SL (slice) direction, appropriate intensities of the MPG pulse can be determined to differentiate signals in blood vessels traveling in the HF direction satisfactorily.

An intensity and a variation width and variation range of an intensity of an MPG pulse can be set arbitrarily by providing instruction information to the pulse sequence setting unit 45 through operation of the input device 33.

According to the DWI-Prep sequence like this, the DWI-Prep scan is performed and artery data are depicted as a blood flow image with arteriovenous separation by the image reconstruction unit 42 and the blood flow image generating unit 44, pieces of image data of arteries corresponding to mutually different intensities of DWI can be obtained. The intensity of artery signals acquired with a high DWI intensity becomes high, on the contrary, the intensity of artery signals acquired with a low DWI intensity becomes low. For this reason, artery data with arteriovenous separation depend on a DWI intensity.

Therefore, by automatic image processing, such as threshold processing, to artery data through arteriovenous separation with each intensity of DWI or user's selection of artery data with visual observation, image data with satisfactorily arteriovenous separation can be selected. Consequently, an appropriate intensity of an MPG pulse can be determined to obtain image data with satisfactorily arteriovenous separation.

An intensity of an MPG pulse can be determined, for example, by selecting a blood flow image where target vessels are depicted appropriately from plural blood flow images, acquired with mutually different intensities of DWI, displayed on the display unit 34 through operation of the input device 33. Therefore, the pulse sequence setting unit 45 is configured to obtain a DWI intensity (an intensity of an MPG pulse) used for imaging a selected blood flow image in response to selection information of a blood flow image from the input device 33. Alternatively, an intensity of an MPG pulse may be inputted as a numeric value into the pulse sequence setting unit 45 through operation of the input device 33.

By the way, scroll acquisition of data by an imaging scan is known to be able to improve effect of an MPG pulse. Therefore, it is preferable to perform scroll acquisition of data in an imaging scan. In addition, it is preferable to match conditions of an imaging sequence for a DWI-Prep scan to that used for an imaging scan as possible. For this purpose, the pulse sequence setting unit 45 is configured to generate a two-dimensional imaging sequence for scroll acquisition of data under a DWI-Prep scan when the pulse sequence setting unit 45 receives instruction for scroll acquisition from the input device 33.

Figure 8:
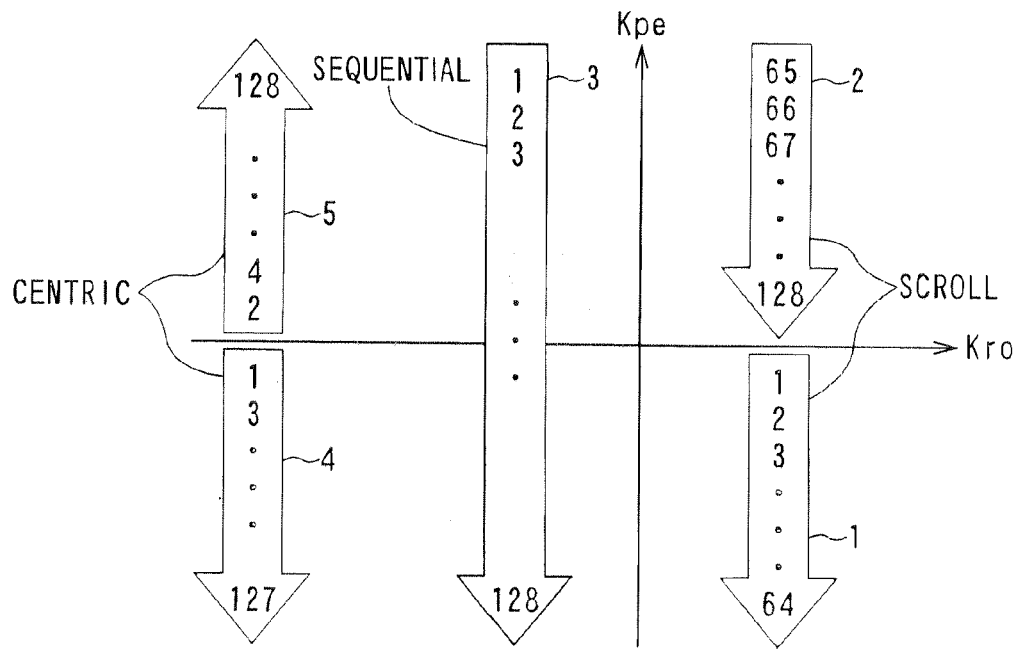
FIG. 8 is a diagram indicating an order for arranging ECHO data acquired by a scroll acquisition in k-space.

FIG. 8 is a diagram indicating an order for arranging ECHO data acquired by a scroll acquisition in k-space.

FIG. 8 represents k-space. That is, in FIG. 8, the ordinate denotes a phase encode direction (Kpe) and the abscissa denotes a readout direction (Kro). As shown in FIG. 8, data are acquired towards the arrow 1 and the arrow 2 under the scroll acquisition. When 128 pieces of data are to be acquired in a PE direction for example, pieces of data are acquired in order of the number described inside of the arrow 1 and the arrow 2 under the scroll acquisition. More specifically, the pieces of data are acquired outward from the vicinity of the center in K-space along the arrow 1. Then, the pieces of data are acquired from a position away from the center of K-space toward the center of K-space along the arrow 2.

By acquiring data of the center of K-space following to application of an MPG pulse in this way, effect of the MPG pulse can be improved. The modification in effect of an MPG pulse based on an order of data acquisition can be obtained not only in imaging by a balanced SSFP sequence but also in imaging under a PROPELLER method. In case of using a sequence such as an FSE sequence, an FASE sequence or an EPI sequence, it is suitable to set the time between application timing of an MPG pulse and acquisition timing for data of the center of K-space to the optimum TE (echo time) by which effect of an MPG pulse is improved.

Note that, as well as the scroll acquisition mentioned above, data can be acquired by sequential acquisition for acquiring the data in one direction in K-space as shown by the arrow 3 in FIG. 8 or by centric acquisition for acquiring data in a positive and negative area alternately from the vicinity of the center of K-space toward a side away from the center of K-space as shown by the arrows 4 and 5. Numbers described inside the arrows 3, 4 and 5 show an acquisition order of 128 pieces of data respectively.

A sequence for an imaging scan is also set in the pulse sequence setting unit 45. The sequence for the imaging scan also consists of a DWI sequence and an imaging sequence.

Figure 9:
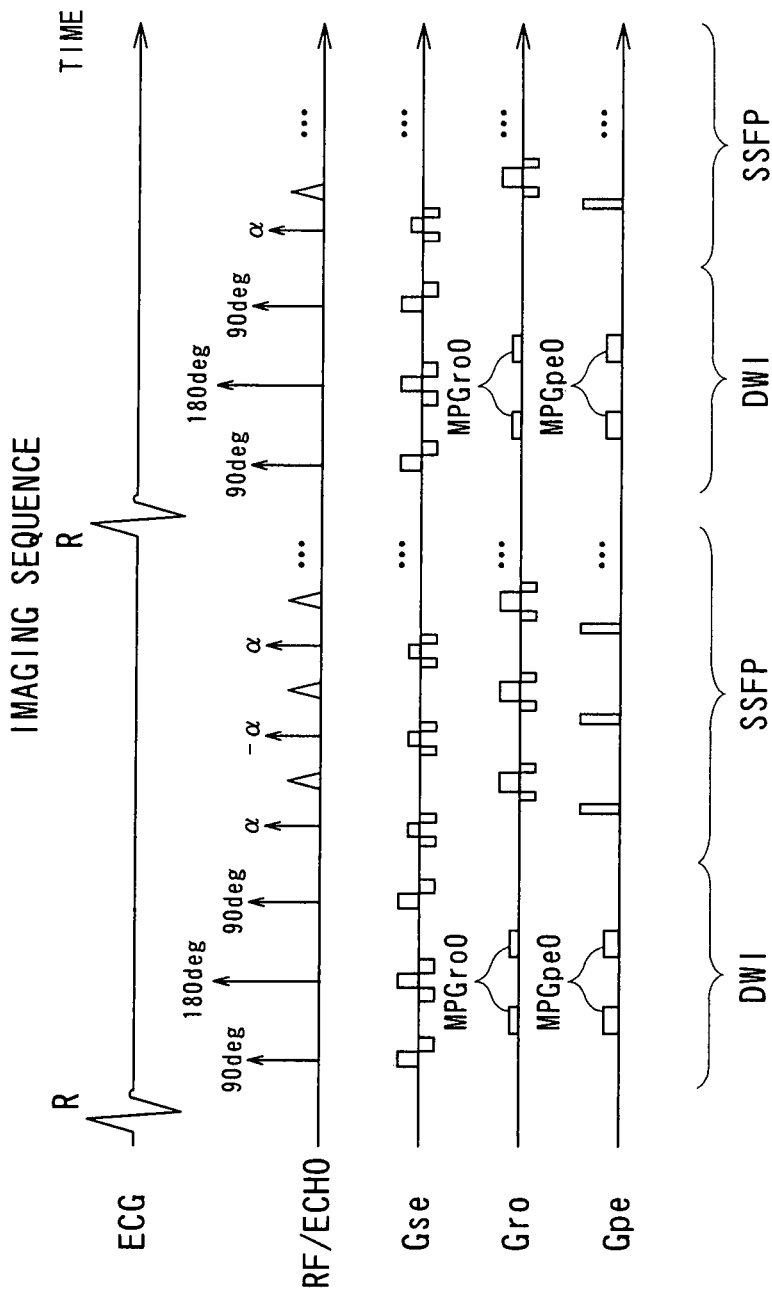
FIG. 9 is a diagram showing an example of a sequence for an imaging scan set in the pulse sequence setting unit shown in FIG. 2.

FIG. 9 is a diagram showing an example of a sequence for an imaging scan set in the pulse sequence setting unit 45 shown in FIG. 2.

In FIG. 9, ECG denotes an ECG signal, RF/ECHO denotes RF signals and ECHO data, Gse denotes a gradient magnetic field for slice encoding, Gro denotes a gradient magnetic field for readout and Gpe denotes a gradient magnetic field for phase encoding respectively. The pulse sequence setting unit 45 sets a sequence for an imaging scan as shown in FIG. 9 for example. The sequence for the imaging scan has a DWI sequence and an imaging sequence following the DWI sequence.

The DWI sequence for the imaging scan is set so that an MPG pulse having intensities determined in three axis directions by the DWI-Prep scan is applied as gradient magnetic field pulses. The imaging sequence for the imaging scan can use an arbitrary sequence for acquiring three-dimensional data. Note that, as described above, if an FSE sequence to perform a balanced SSFP sequence or a PROPELLER method is used as the imaging sequence, a blood flow image can be obtained without depending on travel directions of blood vessels.

Further, from the perspective of setting an appropriate DWI intensity, it is preferable that a sequence as equivalent to the imaging sequence for the DWI-Prep scan as possible is used as the imaging sequence for imaging scan. It is preferable to use a sequence for two-dimensional data acquisition in the DWI-prep scan, and to use a sequence for three-dimensional data acquisition of which the other imaging conditions are same as those of the imaging sequence for the DWI-prep scan in the imaging scan.

FIG. 9 shows an example of setting a balanced SSFP sequence as the imaging sequence for the imaging scan. Therefore, the balanced SSFP sequence is set following to a DWI sequence.

The sequence for the imaging scan consisting of the DWI sequence and the balanced SSFP sequence is performed in synchronization with an ECG signal by using an R wave of the ECG signal as a trigger for example. The Balanced SSFP sequence is preferably set to a single shot sequence suitable for acquiring a blood flow image and an $\alpha°$ pulse and a $-\alpha°$ pulse are applied repeatedly according to the number of pieces of echo data to be acquired. In addition, A pre-pulse (not shown) for various purposes such as a fat saturation pulse is applied subsequently to the first $\alpha°$ pulse as needed.

Then, the DWI sequence is set prior to echo data acquisition under the balanced SSFP sequence. In the DWI sequence, a 90-degree excitation pulse, a subsequent 180-degree refocus pulse and a 90-degree longitudinal magnetization recovery pulse are applied. In addition, MPG pulses are applied before and after the 180-degree refocus pulse. The MPG pulses are applied with intensities determined by the DWI-Prep scan in desired directions of a slice encode direction, a readout direction and a phase encode direction. FIG. 9 shows an example that a readout direction MPG pulse (MPGro0) and a phase encode direction MPG pulse (MPGpe0) are applied while a slice encode direction MPG pulse (MPGse0) is not applied.

Then, with spins dispersed (spoiled) due to diffusion of water molecules in tissues by application of the MPG pulses, echo data is acquired by application of the $\alpha°$ and $-\alpha°$ pulses and the gradient magnetic field pulse of the balanced SSFP sequence.

Further, by quickening and delaying acquisition timings of the echo data according to an ECG waveform, a blood flow image with arteriovenous separation can be generated from echo data acquired in a single heart rate. For the purpose, the pulse sequence setting unit 45 is configured to set an imaging condition in which acquisition timings of echo data are scrolled to timings suitable for generating a blood flow image with arteriovenous separation in response to an instruction to scroll an acquisition timing of echo data from the input device 33.

Figure 10:
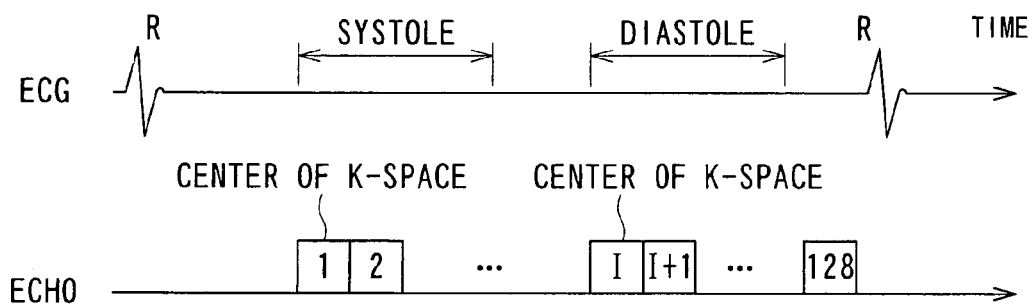
FIG. 10 is a diagram showing an example of timings for acquiring ECHO data set in the pulse sequence setting unit shown in FIG. 2.

FIG. 10 is a diagram showing an example of timings for acquiring ECHO data set in the pulse sequence setting unit 45 shown in FIG. 2.

In FIG. 10, each abscissa denotes time, ECG denotes an ECG signal and ECHO denotes timings for acquiring ECHO data respectively. In the balanced SSFP sequence, approximately 128 pieces of data are acquired between adjacent R waves of an ECG signal (around 1000 ms). When data acquisition timings (cardiac time phase) are scrolled so that data near the center of K-space is acquired in each section of a systole and a diastole between adjacent R waves of an ECG signal, data are acquired with blood flow signals from arteries suppressed in the systole while data are acquired with blood flow signals from arteries unsuppressed in the diastole. Therefore, by calculating a difference between pieces of data acquired in the systole and the diastole respectively, a blood flow image of arteries with arteriovenous separation can be obtained from data acquired in a single heart rate.

According to an example shown in FIG. 10, acquisition timings of pieces of data acquired from the first are set in a systole while those acquired from I-th are set in a diastole. Both of the first acquired data and the I-th acquired data are set to pieces of data of the center of K-space.

Next, the operation and action of a magnetic resonance imaging apparatus 20 will be described.

Figure 11:
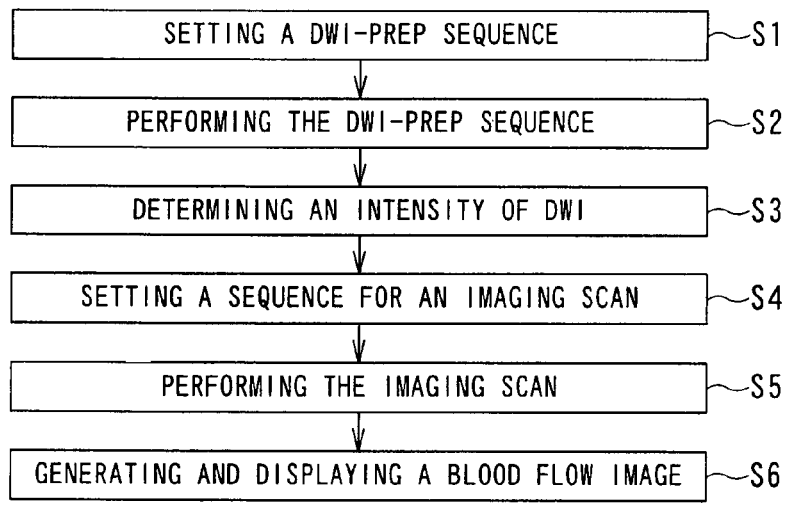
FIG. 11 is a flowchart showing an example of flow for acquiring a blood flow image with the magnetic resonance imaging apparatus shown in FIG. 1.

FIG. 11 is a flowchart showing an example of flow for acquiring a blood flow image with the magnetic resonance imaging apparatus 20 shown in FIG. 1. The symbols including S with a number in FIG. 3 indicate each step of the flowchart. Here, a case of generating a blood flow image through subtraction processing by DWI with application of an MPG pulse will be described.

First in step S1, a DWI-Prep sequence is set by the pulse sequence setting unit 45. Specifically, intensities, respective variation widths of the intensities, respective variation ranges of the intensities (or respective numbers of times of changes of the intensities) of an MPG pulse in three axis directions and a type of imaging sequence are inputted into the pulse sequence setting unit 45 from the input device 33. The intensities, the respective variation widths of the intensities, the respective variation ranges of the intensities (or the respective numbers of times of changes of the intensities) of the MPG pulse in the three axis directions are determined depending on travel directions of blood vessels respectively so that the blood vessels can be imaged more satisfactorily. When the imaging sequence is a balanced SSFP sequence or a sequence under a PROPELLER method, information instructing which of a scroll acquisition, a sequential acquisition or a centric acquisition should be chosen as a data acquisition method is inputted into the pulse sequence setting unit 45 from the input device 33. Alternatively, when the imaging sequence is another sequence, values including a TE value are inputted into the pulse sequence setting unit 45 from the input device 33.

In case of generating a blood flow image from data in a single heart rate with scrolling data acquisition timings in the imaging scan, instructions from the input device 33 are provided to the pulse sequence setting unit 45 so that data acquisition timings in the imaging sequence of the DWI-Prep sequence are set to those for the imaging scan.

Then, the pulse sequence setting unit 45 generates a DWI-Prep sequence as shown in FIG. 6 according to instructions from the input device 33. The pulse sequence setting unit 45, for example, sets a two-dimensional single shot balanced SSFP sequence as the imaging sequence of the DWI-prep sequence. The DWI-Prep sequence set as the single shot multi DWI sequence is provided to the sequence controller control unit 40.

Next in step S2, the DWI-prep scan is performed. For this purpose, an object P is set on the bed 37 and a static magnetic field is generated in an imaging area of the static magnetic field magnet 21 (super conductive magnet) excited by static magnetic field power supply 26. When an instruction to perform the DWI-Prep scan from the input device 33 is provided to the sequence controller control unit 40, the sequence controller control unit 40 drives and controls the sequence controller 31 by providing the DWI-Prep sequence to the sequence controller 31.

Then, the sequence controller 31 forms an X-axis gradient magnetic field Gx, a Y-axis gradient magnetic field Gy and a Z-axis gradient magnetic field Gz and generates RF signals in the imaging area where the object P is set by driving the gradient power supply 27, the transmitter 29 and the receiver 30 according to the DWI-Prep sequence received from the sequence controller control unit 40. Specifically, the transmitter 29 transmits the RF signals to the RF coil 24 sequentially according to the DWI-Prep sequence, and the RF coil 24 transmits the RF signals to the object P.

MR signals generated in a selected slice in the object P due to the transmitted RF signals are received by the RF coil 24. When the MR signals are received by the RF coil 24, the receiver 30 receives the MR signals from the RF coil 24 to perform various signal processing including pre-amplification, intermediate frequency conversion, phase detection, low-frequency amplification and filtering. The receiver 30 generates raw data which are the MR signals of digital data by A/D conversion of the MR signals. The receiver 30 provides the generated raw data to the sequence controller 31.

This acquisition of raw data is performed in synchronization with ECG based on an ECG signal acquired by the ECG unit 38. Herewith, pieces of raw data corresponding to a systole and a diastole of the myocardium are acquired respectively.

The sequence controller 31 provides the raw data received from the receiver 30 to the sequence controller control unit 40, and the sequence controller control unit 40 arranges the raw data obtained by the DWI-Prep scan as K-space data in K-space formed in the K-space database 41.

Then, the image reconstruction unit 42 reconstructs three dimensional image data of the object P by reading the K-space data from the K-space database 41 and performing a predetermined image reconstruction processing such as three-dimensional Fourier transformation. The image reconstruction unit 42 the writes three dimensional image data into the image database 43. Then, the blood flow image generating unit 44 reads pieces of 3D image data corresponding to a diastole and a systole of the myocardium respectively from the image database 43, cancels vein data by subtraction processing to the pieces of 3D image data and depicts artery data as a blood flow image. Thus blood flow images corresponding to the respective intensities of the MPG pulse are depicted. The depicted blood flow images are displayed on the display unit 34.

Since the blood flow images displayed on the display unit 34 are obtained with the MPG pulses having mutually different intensities respectively, depiction accuracies of arteries are different between the blood flow images. In addition, since the intensities of the MPG pulses are changed in three axis directions depending on travel directions of blood vessels, a blood flow image depicting arteries satisfactorily exists in the acquired plural blood flow images. Especially when data was acquired with a scroll acquisition, effect of the MPG pulse on the blood flow image is improved.

Then, in Step S3, the optimum intensity of DWI to depict a blood flow image, which is a combination of intensities of an MPG pulse in three axis directions, is determined. The intensity of DWI can be determined by selecting a blood flow image depicting target blood vessels most satisfactorily with arteriovenous separation from multiple blood flow images displayed on the display unit 34 through user's operation of the input device 33 for example. When the user selects one blood flow image, selection information of blood flow image is provided from the input device 33 to the pulse sequence setting unit 45. The pulse sequence setting unit 45 obtains the combination of the intensities of the MPG pulse in three axis directions corresponding to the selected blood flow image from information concerning imaging conditions attached to blood flow image data for example.

Then, in Step S4, a sequence for the imaging scan is set in the pulse sequence setting unit 45. The sequence for the imaging scan has a DWI sequence and an imaging sequence. An intensity of an MPG pulse in the DWI sequence is set to the intensity determined in step S3. The imaging sequence for the imaging scan uses a sequence equivalent to that in the DWI-Prep sequence as possible. Therefore, for example, the pulse sequence setting unit 45 sets a three-dimensional single shot balanced SSFP sequence as the imaging sequence for the imaging scan.

Consequently, a sequence for the imaging scan as shown in FIG. 9 is generated in the pulse sequence setting unit 45. Further, a scroll of data acquisition timings and an order of data acquisition are set and reflected on the imaging sequence for the imaging scan in the pulse sequence setting unit 45 according to instructing information from the input device 33. The imaging sequence for the imaging scan generated ultimately is provided from the pulse sequence setting unit 45 to the sequence controller unit 40.

Then, in Step S5, the imaging scan is performed. Specifically, when an instruction to start the imaging scan is provided from the input device 33 to the sequence controller unit 40, the sequence controller unit 40 drives and controls the sequence controller 31 by providing the sequence for the imaging scan to the sequence controller 31. Consequently, the imaging scan is performed and K-space data acquired by the imaging scan are arranged in K-space formed in the K-space database 41.

Then, in Step S6, a blood flow image is generated from data acquired by the imaging scan and is displayed on the display unit 34. Specifically, arteries data with arteriovenous separation are depicted as the blood flow image through image reconstruction processing by the image reconstruction unit 42 and subtraction processing of 3D image data by the blood flow image generating unit 44, and are displayed on the display unit 34.

Since the blood flow image displayed on the display unit 34 is imaged with optimizing the intensities of the MPG pulse in the three axis directions depending on the travel directions of the blood vessels, the blood flow image depicts the arteries very satisfactorily. Especially when data is acquired under the scroll acquisition, the blood flow image shows an improved effect of the MPG pulse. In addition, when the acquisition timings of data near the center of K-space are scrolled into the diastole and the systole, the blood flow image depicting the arteries satisfactorily as described above can be generated from only data acquired in a single heart rate.

That is, the magnetic resonance imaging apparatus 20 as mentioned above applies a flow selective gradient magnetic field pulse for compensating a blood flow or accelerating flow void effect and also performs an imaging scan for a no-contrast-enhanced MRA using a sequence without dependence on travel directions of target blood vessels.

Further, as needed for a no-contrast-enhanced MRA, the magnetic resonance imaging apparatus 20 performs a DWI-Prep scan which is a preparation scan for single shot multi DWI for imaging with changing an intensity of DWI (an MPG pulse) as an example of flow selective gradient magnetic field pulse, like as an ECG-Prep scan which is a preparation scan performed with changing parameters, prior to an imaging scan. Thus, the magnetic resonance imaging apparatus 20 measures an intensity of an MPG pulse suitable to depict target blood vessels with arteriovenous separation in advance. Then, the magnetic resonance imaging apparatus 20 performs a 3D scan using an imaging sequence such as a SSFP sequence with applying an MPG pulse having a determined intensity suitable for 3D imaging. Accordingly, by the magnetic resonance imaging apparatus 20, it is possible to obtain a 3D image of blood vessels with satisfactory arteriovenous separation.

Especially in the magnetic resonance imaging apparatus 20, intensities of an MPG pulse applied as a flow selective gradient magnetic field pulse can be changed arbitrarily in three axis directions. Further, a sequence without dependence on directionality of blood flows can be used as an imaging sequence. For this reason, according to the magnetic resonance imaging apparatus 20, it is only necessary to set an intensity of an MPG pulse depending on travel directions of blood vessels in order to improve arteriovenous separation performance so that an intensity of a signal from a blood flow having a high-velocity in a systole is suppressed to increase a difference between respective signals from a blood flow in a diastole and a systole for example.

Therefore, the magnetic resonance imaging apparatus 20 has no necessity to increase an ETS of an FASE method or an SSFP method in order to improve arteriovenous separation performance. As a result, the magnetic resonance imaging apparatus 20 can achieve satisfactory arteriovenous separation of blood vessels having higher velocities, thereby achieving arteriovenous separation without dependence on a velocity of a blood flow. In addition, the magnetic resonance imaging apparatus 20 can also improve flexibility for setting an imaging sequence.

Additionally, in the magnetic resonance imaging apparatus 20, when a sequence without dependence on directionality of blood flows is used as an imaging sequence, a depiction performance of blood flows can be improved by satisfactory arteriovenous separation of blood vessels traveling in arbitrary directions. Especially in case of performing arteriovenous separation of blood flows having low velocities like as a lower limb MRA, a dephasing pulse needed to be applied in an RO direction conventionally. For this reason, a depiction performance of blood vessels depended on travel directions of the blood vessels. To the contrary, the magnetic resonance imaging apparatus 20 can perform satisfactory arteriovenous separation even of blood flows having low velocities like as a lower limb MRA.

Further, the magnetic resonance imaging apparatus 20 can also determine an optimum intensity, depending on a blood flow velocity, of a flow selective gradient magnetic field pulse such as an MPG pulse to maximize a blood-flow signal from target vessels in advance by a preparation scan such as a DWI-Prep scan without changing an imaging sequence.

What is claimed is:

1. A magnetic resonance imaging (MRI) apparatus comprising:
    an MRI sequence controller configured to perform an imaging sequence wherein imaging data is acquired after performing a pre-pulse sequence which applies a gradient magnetic field pulse for flow selection to perform one of (a) compensating a flow and (b) facilitating flow void effect in a blood vessel of an object, said imaging data being acquired by performing an MRI pulse sequence which includes a radio frequency excitation pulse and which is independent from a blood travel direction of a target blood vessel; and
    a blood flow image generating unit configured to generate a non-contrast-enhanced blood flow image of the object based on magnetic resonance signals acquired by the imaging sequence,
    wherein the MRI sequence controller is configured to control the pre-pulse sequence so that (a) the gradient magnetic field pulse for flow selection in the pre-pulse sequence is applied in a blood flow travel direction of the target blood vessel, and (b) a longitudinal magnetization recovery pulse in the pre-pulse sequence is applied after the gradient magnetic field pulse for flow selection is applied, the longitudinal magnetization recovery pulse transforming transverse magnetization of spins into longitudinal magnetization.

2. A magnetic resonance imaging apparatus according to claim 1, wherein
    said MRI sequence controller is configured to apply the longitudinal magnetization recovery pulse previous to performing the MRI pulse sequence that is independent from the blood travel direction of the target blood vessel.

3. A magnetic resonance imaging apparatus according to claim 1, wherein said MRI sequence controller is configured to acquire a first echo signal set by performing a first three dimensional scan at a first cardiac time phase of the object and a second echo signal set by performing a second three dimensional scan at a second cardiac time phase of the object, at least one of the first and the second three dimensional scans being performed during said MRI pulse sequence and thus subsequent to applying the gradient magnetic field pulse for flow selection during the pre-pulse sequence, and said blood flow image generating unit is configured to generate a subtraction image by subtraction between a first image and a second image, the first and the second images being generated based on the first and the second echo signal sets, respectively.

4. A magnetic resonance imaging apparatus according to claim 1, wherein
said MRI sequence controller is configured to apply a pre-pulse serving as the gradient magnetic field pulse for the flow selection to either of (a) a blood flow in an artery and (b) a blood flow having a fast flow velocity.

5. A magnetic resonance imaging apparatus according to claim 1, wherein
said MRI sequence controller is configured to apply a motion probing gradient pulse as the gradient magnetic field pulse for flow selection.

6. A magnetic resonance imaging apparatus according to claim 1, wherein
said MRI sequence controller is configured to use during said MRI pulse sequence either of (a) a sequence for aligning a phase of a transverse magnetization in every repeated excitation and (b) a balanced SSFP sequence for acquiring signals in a state of Steady State Free Precession as the sequence independent from the blood travel direction of the target blood vessel.

7. A magnetic resonance imaging apparatus according to claim 1, further comprising:
said MRI sequence controller being configured to perform a preparation scan with intensities of plural types of gradient magnetic field pulses for flow selections; and
a reference blood flow image generating unit configured to generate blood flow images for reference based on data corresponding to each intensity of the plural types of the gradient magnetic field pulses for the flow selections, the data being acquired by the preparation scan,
wherein said MRI sequence controller is configured to perform the pre-pulse sequence with an intensity of a gradient magnetic field pulse for a flow selection used for a preparation scan for a reference blood flow image selected from the blood flow images for the reference.

8. A magnetic resonance imaging apparatus according to claim 3, wherein
said MRI sequence controller is configured to acquire MRI data in a vicinity of a center of k-space during diastole serving as the first cardiac time phase and during systole as the second cardiac time phase.

9. A magnetic resonance imaging apparatus according to claim 5, further comprising
an imaging condition setting unit configured to be able to change intensities of the motion probing gradient pulse in three directions of a gradient magnetic field direction for slice encoding, a gradient magnetic field direction for phase encoding and a gradient magnetic field direction for readout.

10. A magnetic resonance imaging apparatus according to claim 9, wherein
said imaging condition setting unit is configured to be able to change the intensities of the motion probing gradient pulse in accordance with the blood travel direction of the target blood vessel.

11. A magnetic resonance imaging apparatus according to claim 1, wherein
said MRI sequence controller is configured to use an MRI pulse sequence according to a PROPELLER method for filling k-space by acquiring mutually parallel data groups forming a blade in one repetition time and rotating the blade every repetition time as the sequence independent from the blood travel direction of the target blood vessel.

12. A magnetic resonance imaging apparatus according to claim 1, wherein
said MRI sequence controller is configured to apply the gradient magnetic field pulse for flow selection subsequent to applying an excitation pulse and previous to applying a refocus pulse.

13. A magnetic resonance imaging apparatus comprising:
an MRI sequence controller configured to perform an imaging sequence wherein imaging data is acquired after performing a pre-pulse sequence which applies a gradient magnetic field pulse for flow selection to serve one of (a) a purpose of compensating a flow and (b) another purpose of facilitating flow void effect in a blood vessel of an object, said imaging data being acquired by performing an MRI pulse sequence which includes a radio frequency excitation pulse and which is independent from a blood travel direction of a target blood vessel; and
a blood flow image generating unit configured to generate a non-contrast-enhanced blood flow image of the object based on magnetic resonance signals acquired by the imaging sequence,
wherein the MRI sequence controller is configured to control the pre-pulse sequence so as to include a longitudinal magnetization recovery pulse that transforms a transverse magnetization of spins into a longitudinal magnetization and is applied after application of the gradient magnetic field pulse for flow selection.

14. A magnetic resonance imaging (MRI) apparatus comprising:
an MRI sequence controller configured to perform an imaging sequence wherein imaging data is acquired after performing a pre-pulse sequence which applies a gradient magnetic field pulse for flow selection to perform one of (a) compensating a flow and (b) facilitating flow void effect in a blood vessel of an object, said imaging data being acquired by performing an MRI pulse sequence which includes a radio frequency excitation pulse and which is independent from a blood travel direction of a target blood vessel; and
a blood flow image generating unit configured to generate a non-contrast-enhanced blood flow image of the object based on magnetic resonance signals acquired by the imaging sequence,
wherein the MRI sequence controller is configured to control the pre-pulse sequence so that the gradient magnetic field pulse for flow selection in the pre-pulse sequence is applied in a blood flow travel direction of the target blood vessel.

* * * * *